(12) United States Patent
Matsuo et al.

(10) Patent No.: US 12,245,353 B2
(45) Date of Patent: Mar. 4, 2025

(54) IRRADIATOR AND PLASMA APPARATUS

(71) Applicant: SEKISUI CHEMICAL CO., LTD., Osaka (JP)

(72) Inventors: Tatsuya Matsuo, Kyoto (JP); Yu Nagahara, Kyoto (JP); Takaya Oshita, Ibaraki (JP); Naomichi Saitou, Kyoto (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 208 days.

(21) Appl. No.: 17/920,514

(22) PCT Filed: Mar. 22, 2021

(86) PCT No.: PCT/JP2021/011722
§ 371 (c)(1),
(2) Date: Oct. 21, 2022

(87) PCT Pub. No.: WO2021/215170
PCT Pub. Date: Oct. 28, 2021

(65) Prior Publication Data
US 2023/0156899 A1    May 18, 2023

(30) Foreign Application Priority Data

Apr. 24, 2020   (JP) .................. 2020-077504

(51) Int. Cl.
*H05H 1/26* (2006.01)
*A61B 18/04* (2006.01)

(52) U.S. Cl.
CPC .............. *H05H 1/26* (2013.01); *A61B 18/042* (2013.01); *H05H 2242/20* (2021.05); *H05H 2245/32* (2021.05)

(58) Field of Classification Search
CPC .............. H05H 1/3484; H05H 1/3457; H05H 2242/20; H05H 2242/22; H05H 1/2481; H05H 1/3463; H05H 1/44; H05H 1/32
See application file for complete search history.

(56) References Cited

U.S. PATENT DOCUMENTS

2009/0321026 A1* 12/2009 Medoff .................. D21H 21/28
                                                                162/158
2010/0042088 A1    2/2010 Arts
(Continued)

FOREIGN PATENT DOCUMENTS

CN        108684129      10/2018
DE   10 2008 018 827    10/2009
(Continued)

OTHER PUBLICATIONS

International Search Report issued Jun. 1, 2021 in corresponding International Application No. PCT/JP2021/011722.
(Continued)

*Primary Examiner* — Monica C King
(74) *Attorney, Agent, or Firm* — Wenderoth, Lind & Ponack, L.L.P.

(57) ABSTRACT

An irradiator includes: a piezoelectric transformer accommodated in a housing; a first electrode connected to the piezoelectric transformer, to which a voltage is applied from the piezoelectric transformer; and an irradiation opening that ejects at least one of a plasma generated by the first electrode and an active gas generated by the plasma. At least a part of the first electrode is located between the piezoelectric transformer and the irradiation opening.

8 Claims, 4 Drawing Sheets

(56) References Cited

U.S. PATENT DOCUMENTS

2016/0329192 A1  11/2016  Sieber et al.
2018/0249569 A1   8/2018  Weilguni et al.

FOREIGN PATENT DOCUMENTS

| DE | 102008018827 B4 * | 5/2010 | ........... H05H 1/2475 |
|---|---|---|---|
| JP | 2013-197140 | 9/2013 | |
| JP | 2015-522901 | 8/2015 | |
| JP | 2016-510483 | 4/2016 | |
| JP | 2017-508485 | 3/2017 | |
| JP | 2020-405 | 1/2020 | |
| WO | 2013/164406 | 11/2013 | |
| WO | 2014/115050 | 7/2014 | |
| WO | 2015/087287 | 6/2015 | |

OTHER PUBLICATIONS

International Preliminary Report on Patentability issued Oct. 25, 2022 in corresponding International (PCT) Application No. PCT/JP2021/011722.

Extended European Search Report issued Apr. 18, 2024 in corresponding European Patent Application No. 21792022.2.

Hyun Kim et al., "Atmospheric pressure argon plasma jet using a cylindrical piezoelectric transformer", Applied Physics Letters, American Institute of Physics, vol. 95, No. 21, Nov. 2009, pp. 211501-1 through 211501-3.

Michal Babij et al., "Atmospheric pressure plasma jet with high-voltage power supply based on piezoelectric transformer", Review of Scientific Instruments, vol. 85, No. 5, May 2014, pp. 054703-1 through 054703-5.

* cited by examiner

IRRADIATOR AND PLASMA APPARATUS

TECHNICAL FIELD

The present invention relates to an irradiator and a plasma apparatus.

BACKGROUND ART

A technique of using a plasma for wound cure, etc. has been proposed (see JP2017-508485A). A tool for curing wound disclosed in JP2017-508485A directs a plasma flow to a wound part to be cured to cure the wound with the plasma. The tool for curing wound of JP2017-508485A comprises a housing, and a piezoelectric transformer accommodated in the housing. In the tool for curing wound of JP2017-508485A, the piezoelectric transformer uses a high voltage generated a high voltage end to generate a plasma.

DISCLOSURE OF THE INVENTION

When a plasma is generated at the high voltage end of the piezoelectric transformer, a distal end portion of the tool, which generates a plasma for irradiation, has a large thickness in accordance with a thickness of the piezoelectric transformer. This makes it difficult to apply the tool to an application in which the distal end portion is inserted into a narrow space, e.g., dental treatment where the distal end portion of the tool is inserted into a mouth of a person or animal.

The object of the present invention is to provide an irradiator and a plasma apparatus capable of effectively solving such a problem.

An irradiator according to the present invention comprises: a piezoelectric transformer accommodated in a housing; a first electrode connected to the piezoelectric transformer, to which a voltage is applied from the piezoelectric transformer; and an irradiation opening that ejects at least one of a plasma generated by the first electrode and an active gas generated by the plasma; wherein at least a part of the first electrode is located between the piezoelectric transformer and the irradiation opening.

The irradiator according to the present invention may comprise a second electrode opposed to at least a part of the first electrode.

In the irradiator according to the present invention, the second electrode may surround the first electrode from a circumference about an axis of the first electrode.

In the irradiator according to the present invention, the first electrode may have a first end portion positioned oppositely to an end portion connected to the piezoelectric transformer, in a direction in which the axis of the first electrode extends; and the second electrode may surround the first end portion from the circumference about the axis of the first electrode.

In the irradiator according to the present invention, the second electrode may have a dimension larger than a dimension of the first electrode, in a direction in which an axis of the first electrode extends.

In the irradiator according to the present invention, the second electrode may have a dimension smaller than a dimension of the piezoelectric transformer, in a radial direction perpendicular to an axis of the first electrode.

In the irradiator according to the present invention, the first electrode may have a dimension smaller than a dimension of the piezoelectric transformer, in a radial direction perpendicular to an axis of the first electrode.

A plasma apparatus according to the present invention comprises: the aforementioned irradiator; a power source that applies a voltage to the piezoelectric transformer; and a voltage supply line connecting the piezoelectric transformer and the power source.

The irradiator and the plasma apparatus of the present invention can make smaller a thickness of the distal end portion of the irradiator.

MODE FOR CARRYING OUT THE INVENTION

Figure 1:
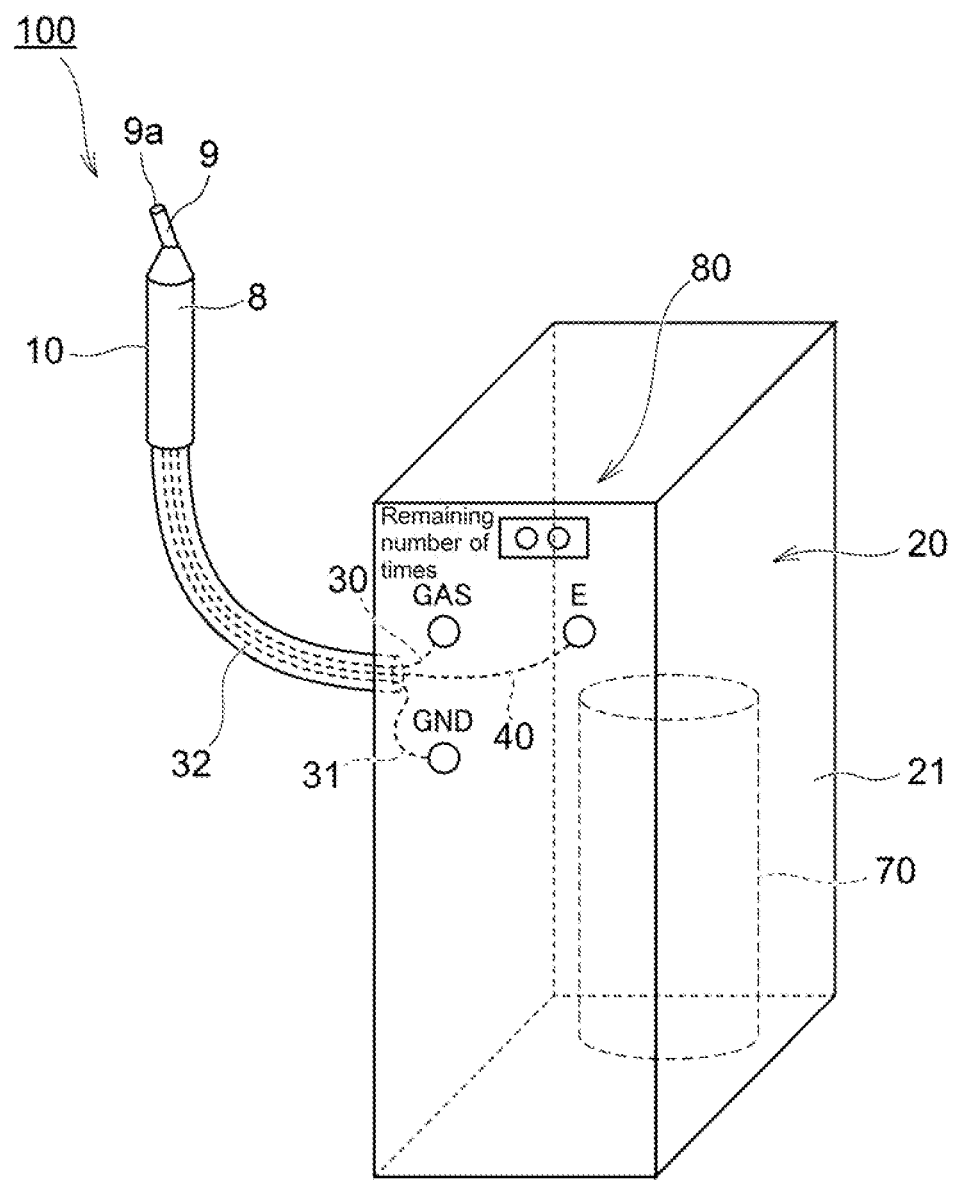
FIG. 1 is a schematic view showing a plasma apparatus according to one embodiment of the present invention.

An embodiment of the present invention will be described herebelow with reference to the drawings. In the drawings attached to the specification, a scale dimension, an aspect ratio and so on are changed and exaggerated from the actual ones, for the convenience of easiness in illustration and understanding.

Further, terms specifying shapes, geometric conditions and their degrees, e.g., "parallel", "perpendicular", "same", etc., and values of a length and an angle are not limited to their strict definitions, but construed to include a range capable of exerting a similar function, unless otherwise specified.

A plasma apparatus of the present invention is a plasma jet irradiation apparatus or an active gas irradiation apparatus. Both the plasma jet irradiation apparatus and the active gas irradiation apparatus generate a plasma. The plasma jet irradiation apparatus directly applies the generated plasma and an active species directly to an irradiation target. The active species is generated by reaction between a gas in the plasma or a gas around the plasma and the plasma. The active species is, for example, active oxygen species or active nitrogen species. The active oxygen species is, for example, hydroxyl radical, singlet oxygen, ozone, hydrogen peroxide, superoxide anion radical, etc. The active nitrogen species is, for example, nitrogen monoxide, nitrogen dioxide, peroxynitrite, dinitrogen trioxide, etc. The active gas irradiation apparatus applies an active gas containing an active species to an irradiation target. The active species is generated by reaction between a gas in the plasma or a gas around the plasma and the plasma.

Figure 2:
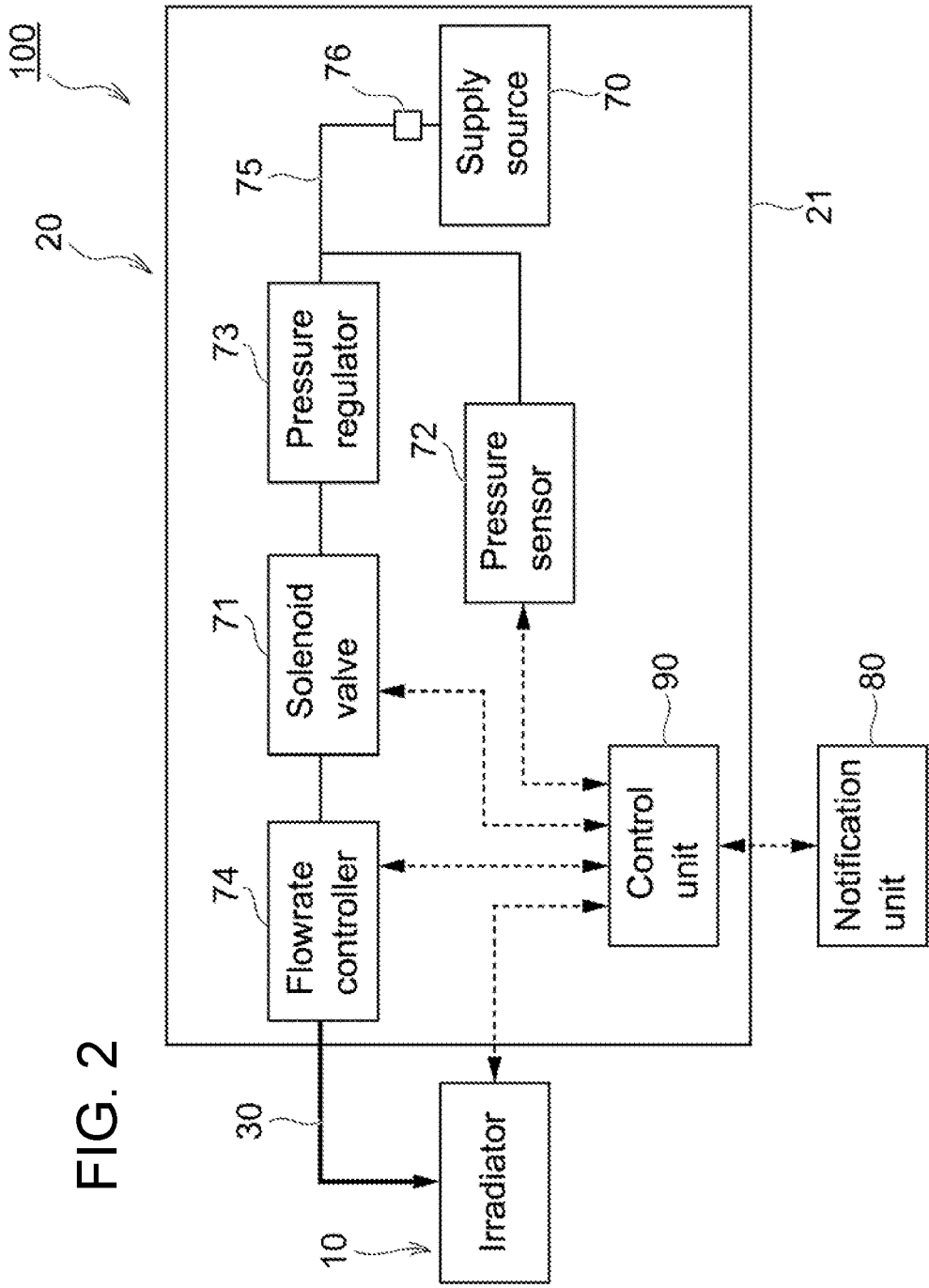
FIG. 2 is a block diagram showing a schematic structure of the plasma apparatus according to one embodiment of the present invention.

An embodiment of the irradiator and the plasma apparatus is described herebelow. The plasma apparatus in this embodiment is an active gas irradiation apparatus, for example. As shown in FIGS. 1 and 2, the active gas irradiation apparatus 100 in this embodiment comprises an irradiator 10, a supply unit 20, a gas pipeline 30, a voltage supply line 40, a supply source 70, a notification unit 80, and a control unit 90 (operation unit).

The irradiator 10 ejects an active gas generated in the irradiator 10. The irradiator 10 is operated by a doctor or the like, and has a shape, a size, and a weight that are easy to operate by human hands. The irradiator 10 is connected to the supply unit 20 through the gas pipeline 30, a ground wire 31, and the voltage supply line 40. In the example shown in FIG. 1, the irradiator 10 comprises an outer cylinder member 8, and a nozzle 9 forming a distal end of the irradiator 10. The nozzle 9 is attached to a distal end of a second electrode 5 described later. The nozzle 9 has therein a flow channel through which an active gas flows. The active-gas flow channel in the nozzle 9 is in communication with a flow channel for a plasma generation gas inside the irradiator 10. When the irradiator 10 has the nozzle 9, the active gas passes through between a first electrode 4 described later and the second electrode 5, and the flow channel inside the nozzle 9 to be ejected from a nozzle irradiation opening 9a positioned at a distal end of the nozzle 9.

The gas pipeline 30 and the voltage supply line 40 are accommodated in a single cable 32. In particular, the voltage supply line 40 connects a piezoelectric transformer 2 described later and an external power source. The power source applies voltage to the piezoelectric transformer 2. The supply unit 20 supplies the irradiator 10 with power and a plasma generation gas. The supply unit 20 accommodates the supply source 70. The supply source 70 accommodates the plasma generation gas. The supply unit 20 is powered by a power source such as a 100-V household power supply. In this case, since the voltage supply line 40 connects the piezoelectric transformer 2 and the supply unit 20, the voltage supply line 40 connects the piezoelectric transformer 2 and the power source through the supply unit 20. Alternatively, the supply unit 20 may incorporate a rechargeable battery as a power source. In this case, the voltage supply line 40 connects the piezoelectric transformer 2 and the power source inside the supply unit 20.

Figure 3:
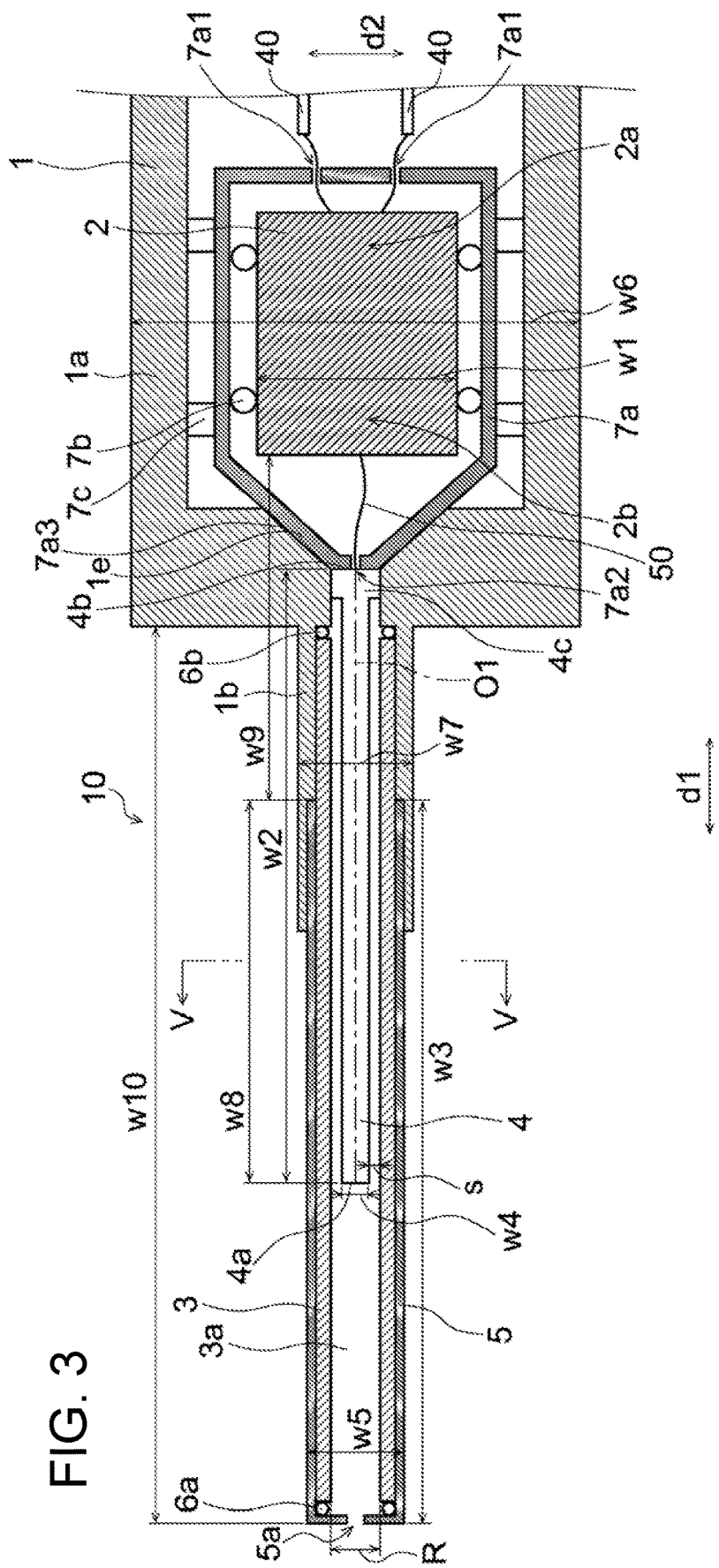
FIG. 3 is a sectional view of an irradiator according to one embodiment of the present invention.
Figure 4:
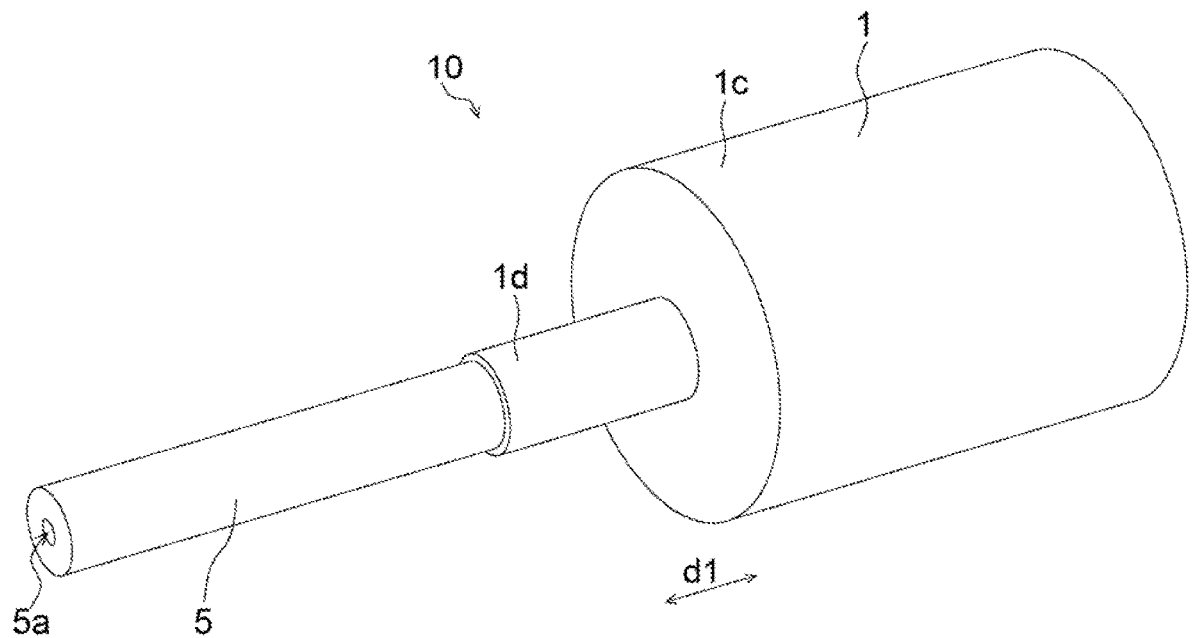
FIG. 4 is a perspective view of the irradiator of FIG. 3.
Figure 5:
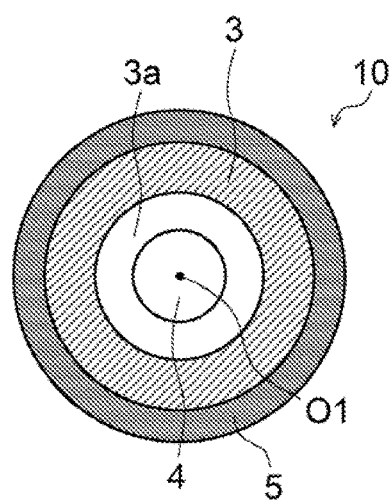
FIG. 5 is a sectional view of the irradiator of FIG. 3, taken along a V-V line.

FIG. 3 is a view showing the irradiator 10, which is a sectional view (longitudinal sectional view) of a plane along a direction in which the irradiator 10 extends, FIG. 4 is a perspective view showing the irradiator of FIG. 3. FIG. 5 is a sectional view showing a section of the irradiator 10 of FIG. 3 taken along a line V-V. In FIGS. 3 to 5, illustration of the outer cylinder member 8 and the nozzle 9 is omitted. As shown in FIG. 3, the irradiator 10 comprises the first electrode 4, and the second electrode 5 opposed at least a part of the first electrode 4. The first electrode 4 has an axis O1. The axis O1 of the first electrode 4 is, for example, a virtual line segment which extends in a direction d1 along which the first electrode 4 extends, and is located within a range where the first electrode 4 is located in the direction d1. Herebelow, the direction d1 along which the axis O1 extends is also referred to as axial direction d1.

In the example shown in FIG. 3, the irradiator 10 further comprises a housing 1, the piezoelectric transformer 2, a tubular dielectric 3, O-rings 6a, 6b, a piezoelectric transformer casing 7, and buffers 7b, 7c.

The piezoelectric transformer 2 boosts a voltage applied thereto. A plasma can be generated by boosting a voltage applied to the piezoelectric transformer 2 from the power source using the piezoelectric transformer 2 to obtain a high voltage, and using the high voltage. In the example shown in FIG. 3, the piezoelectric transformer 2 has an input area 2a that converts the applied voltage to mechanical vibrations, and an output area 2b that convers the vibrations of the input area 2a to a voltage. As shown in FIG. 3, the voltage supply line 40 is connected to the input area 2a. In the example shown in FIG. 3, the voltage supply line 40 extends through a hole 7a1 provided in the piezoelectric transformer casing 7 accommodating the piezoelectric transformer 2. The first electrode 4 described later is connected to the output area 2b. A voltage applied from the external power source through the voltage supply line 40 is converted by the input area 2a to mechanical vibrations. The vibrations of the input area 2a are converted by the output area 2a to a voltage, which is then applied to the first electrode 4. Since the voltage is once converted to the mechanical vibrations and the mechanical vibrations are again converted to the voltage by the piezoelectric transformer 2, the voltage applied from the power source can be boosted, and and the boosted voltage can then be applied to the first electrode 4.

In this embodiment, the piezoelectric transformer 2 is accommodated in the housing 1 described later. In the example shown in FIG. 3, the piezoelectric transformer 2 is accommodated in the piezoelectric transformer casing 7a, and the piezoelectric transformer casing 7a is accommodated in the housing 1.

The piezoelectric transformer 2 has a parallelepiped shape extending in the axial direction d1, for example. A dimension w1 of the piezoelectric transformer 2 in a direction d2 (referred to also as radial direction d2 herebelow) perpendicular to the axis O1 is between 3 cm or more and 20 cm or less, for example.

In the example shown in FIG. 3, the first buffer 7b is provided between the piezoelectric transformer 2 and the piezoelectric transformer casing 7a. The first buffer 7b allows mechanical vibrations of the piezoelectric transformer 2, while defining a positional relationship between the piezoelectric transformer 2 and the piezoelectric transformer casing 7a. A material of the first buffer 7b is not specifically limited, as long as it does not significantly dampen the mechanical vibrations of the piezoelectric transformer 2. The material of the first buffer 7b is an elastically deformable material such as rubber. In addition, in the example shown in FIG. 3, the second buffer 7c is provided between the piezoelectric transformer casing 7a and the housing 1. A material of the second buffer 7c is similar to the material of the first buffer 7b. Although not shown, the irradiator 10 may be free of the second buffer 7c.

The piezoelectric transformer 2 can have a size smaller than another transformer such as a winding trans. Thus, the use of the piezoelectric transformer 2 as a transformer makes it possible that the transformer is accommodated in the housing 1 grasped by a user so that the transformer constitutes a part of the irradiator 10, and at the same time makes it possible that irradiator 10 has a small size.

The first electrode 4 is an electrode that is connected to the piezoelectric transformer 2, to which a voltage for generating a plasma is applied from the piezoelectric transformer 2. When a voltage is applied, the first electrode 4 generates a plasma. At least a part of the first electrode 4 is located between the piezoelectric transformer 2 and an irradiation opening 5a described later of the irradiator 10. In the example shown in FIG. 3, the electrode 4 is entirely located between the piezoelectric transformer 2 and the irradiation opening 5a of the irradiator 10. Thus, when a voltage is applied to the first electrode 4, a plasma is generated between the piezoelectric transformer 2 and the irradiation opening 5a. The first electrode 4 according to this embodiment has a columnar shape extending in the axial direction d1. The first electrode 4 has a first end portion 4a and a second end portion 4b positioned at both ends in the axial direction d1. In the example shown in FIG. 3, the irradiator 10 further comprises a conductive wire 50 connected to the output area 2b of the piezoelectric transformer 2 and the second end portion 4b of the first electrode 4. The first electrode is connected to the output area 2b of the piezoelectric transformer 2 through the conductive wire 50. In the example shown in FIG. 3, the conductive wire 50 extends through a hole 7a2 provided in the piezoelectric transformer casing 7a.

A material of the first electrode 4 is not specifically limited as long as it is an electrically conductive material, and a metal used for an electrode of a known plasma apparatus can be used. The material of the first electrode 4 may be, for example, a metal such as stainless steel, copper, tungsten, or carbon, etc. A material of the conductive wire 50 is not specifically limited, as long as it is an electrically conductive and is sufficiently soft so as not to suppress transmission of mechanical vibrations of the piezoelectric transformer 2 to the first electrode 4.

A voltage applied from the piezoelectric transformer 2 to the first electrode 4 is not specifically limited, as long as it enables generation of a plasma between the first electrode 4 and the second electrode 5. When a plasma is generated by using a gas containing nitrogen as a main component described later, a voltage applied to the first electrode 4 is, for example, between 0.5 kVpp or more and 20 kVpp or less. The voltage applied to the first electrode 4 is more preferably between 2 kVpp or more and 18 kVpp or less, and furthermore preferably between 5 kVpp or more and 15 kVpp or less. Note that "pp" in "kVpp" is an abbreviation for "peak to peak".

The second electrode 5 is an electrode that is opposed to at least a part of the first electrode 4. In the example shown in FIGS. 3 and 5, the second electrode 5 is opposed to a part of the first electrode 4. As an example, the second electrode 5 surrounds the first electrode 4 from a circumference about the axis line O1. In the example shown in FIG. 3, from among the first end portion 4a and the second end portion 4b of the first electrode 4, the second electrode 5 surrounds the first end portion 4a which is positioned oppositely to the end portion 4b in the axial direction d1, the end portion 4b being connected to the piezoelectric transformer 2. In the example shown in FIGS. 3 and 5, the second electrode 5 surrounds a part of the first electrode 4 including the first end portion 4a from a circumference about the axis O1. In this embodiment, the second electrode 5 is a substantially cylindrical electrode that surrounds a part of the circumference of the first electrode 4. In this embodiment, the second electrode 5 is electrically grounded. Although not shown, the second electrode 5 is connected to a grounding wire so as to be electrically grounded.

Since the irradiator 10 comprises the grounded second electrode 5 as well as the first electrode 4 to which a voltage is applied, an electric field for generating a plasma can be more reinforced when a plasma is generated by the first electrode 4. By supplying a plasma generation gas to a space between the first electrode and the second electrode 5 and by applying a voltage to the first electrode 4 opposed to the second electrode 5, electricity is discharged to a space between the first electrode 4 and the second electrode 5 so that the plasma generation gas is ionized to generate a plasma. In this case, it can be said that the first electrode 4 and the second electrode 5 generate a plasma. The plasma is generated between the first electrode 4 and the second electrode 5 opposed to each other.

Since the grounded second electrode 5 is opposed to at least a part of the first electrode 4, in particular, the second electrode 5 surrounds the first electrode 4 from a circumference about the axis O1, an electric field generated by the first electrode 4 can be reduced by the second electrode 5. Thus, electric shock to a user grasping the irradiator 10 can be suppressed. From the viewpoint of suppressing electric shock to a user, a dimension w3 of the second electrode 5 in the axial direction d1 shown in FIG. 3 is preferably larger than a dimension w2 of the first electrode 4 in the axial direction d1. Since a large area of the first electrode 4 is covered with the second electrode 5, the electric shock to a user can be more effectively suppressed. When the electric shock to a user is sufficiently suppressed by the second electrode 5, it is not necessary for the irradiator 10 to have another member having a protective function for suppressing the electric shock to a user, such as the outer cylinder member 8, the nozzle 9, etc. In this case, since another member having a protective function can be omitted, a thickness of the distal end portion positioned on the distal end side of the irradiator 10 can be made thinner.

A material of the second electrode 5 is not specifically limited as long as it is an electrically conductive material, and a metal used for an electrode of a known plasma apparatus can be used. The material of the second electrode 5 may be, for example, a metal such as stainless steel, copper, tungsten, or carbon, etc.

The irradiator 10 further comprises the irradiation opening 5a that ejects at least one of a generated plasma and an active gas generated by the plasma. In FIG. 3, the irradiation opening 5a is provided on an end portion of the second electrode 5 on the distal end side (left side in FIG. 3) of the irradiator 10. The irradiation opening 5a communicates an inner hollow 3a of the tubular dielectric 3 described later with the outside of the irradiator 10.

The tubular dielectric 3 is a member having the inner hollow 3a. In the example shown in FIGS. 3 to 5, the tubular dielectric is a cylindrical member extending in the axial direction d1. As shown in FIGS. 3 and 5, the first electrode 4 is located in the inner hollow 3a of the tubular dielectric 3.

In the example shown in FIGS. 3 and 5, the first electrode 4 is located to be apart from an inner surface of the tubular dielectric 3. The second electrode 5 is located to be in contact with an outer surface of the tubular dielectric 3.

A dielectric material used for a known plasma apparatus can be used as a material of the tubular dielectric 3. The material of the dielectric material 3 is, for example, glass, ceramic, synthetic resin, etc. The lower the dielectric constant of the tubular dielectric 3, the better.

An internal diameter R of the tubular dielectric 3 can be suitably determined in consideration of a dimension w4 of the first electrode 4 in the radial direction d2. The internal diameter R is determined such that a distance s described later is within a desired range.

In a case where the first electrode 4 and the tubular dielectric 3 are spaced apart from each other, the distance s between the outer surface of the first electrode 4 and the inner surface of the tubular dielectric 3 is preferably between 0.05 mm and 5 mm, more preferably between 0.1 mm and 1 mm. When the distance s is equal to or more than the above lower limit value, it is easy for a plasma generation gas of a desired volume to flow therethrough, when the inner hollow 3a of the tubular dielectric 3 is used as a flow channel of the plasma generation gas as described later. When the distance s is equal to or less than the above upper limit value, a plasma can be more efficiently generated so that a temperature of an active gas can be lowered.

The housing 1 is a member grasped by a user and accommodating the piezoelectric transformer 2. In the example shown in FIG. 3, the housing 1 accommodates the piezoelectric transformer casing 7a so as to accommodate the piezoelectric transformer 2. In the example shown in FIGS. 3 to 5, the housing 1 is a substantially cylindrical member extending in the axial direction d1. As an example, the housing 1 has a first portion 1a accommodating the piezoelectric transformer 2, and a second portion 1b accommodating at least a part of the first electrode 4. In the example shown in FIGS. 3 to 5, the first portion 1a and the second potion 1b both have a substantially cylindrical shape extending in the axial direction d1. Although not shown, the first portion 1a and the second portion 1b may have a polygonal cylindrical shape, such as a quadrangular cylindrical shape, a hexagonal cylindrical shape, an octagonal cylindrical shape, etc.

In the example shown in FIG. 3, the first portion 1a has inside thereof an inclination surface 1e that is inclined with respect to the radial direction d2. The piezoelectric transformer casing 7a has a casing inclination surface 7a3 that is inclined with respect to the radial direction d2 to be in contact with the inclination surface 1e. The piezoelectric transformer casing 7a is inserted into the first portion is of the housing 1 from the side of the first portion 1a (left side in FIG. 3) such that the casing inclination surface 7a3 comes into contact with the inclination surface 1e, so that the piezoelectric transformer casing 7a is fixed to the housing 1.

In the example shown in FIG. 3, a part of the second electrode 5 is inserted in the second portion 1b of the housing 1 so that the second portion 1b and the first electrode 5 are in contact with each other. As an example, the housing 1 and the second electrode 5 are fixed to each other by a fixing means, not shown. For example, the housing 1 and the second electrode 5 have screw holes, not shown, and the second electrode 5 is screwed to the housing 1.

In addition, a part of the tubular dielectric 3 is inserted in the second portion 1b of the housing 1 so that the second portion 1b and the tubular dielectric 3 are in contact with each other. In the example shown in FIG. 3, the second electrode 5 is in contact with the tubular dielectric 3 through the O-ring 6a from one side along the axis O1 to restrict movement of the tubular dielectric 3 to the one side along the axis O1 of the tubular dielectric 3. In addition, the housing 1 is in contact with the tubular dielectric 3 through the O-ring 6b from the other side along the axis O1 to restrict movement of the tubular dielectric 3 to the other side long the axis O1. The O-ring 6a, 6b is a member made of a resilient resin, and has an internal diameter in tight contact with an outer circumferential surface of the tubular dielectric 3. Thus, the tubular dielectric 3 is held with its movement along the axial direction d1 being restricted.

The housing 1 may have a part in contact with the first electrode 4, so that t movement of the first electrode 4 may be restricted by the housing 1 in contact with the first electrode 4. In addition, movement of the first electrode 4 may be restricted by the piezoelectric transformer casing 7a in contact with the first electrode 4. In the example shown in FIG. 3, the piezoelectric transformer casing 7a is in contact with the second end portion 4b of the first electrode 4 to restrict movement of the first electrode 4 along the axial direction d1. The first electrode 4 has a larger diameter portion 4c near the first end portion 4b, the larger diameter portion 4c having a largest outward projecting length in the radial direction d2. The housing 1 is in contact with the larger diameter portion 4c to restrict movement of the first electrode 4 along the radial direction d2.

A material of the housing 1 is not specifically limited, but an insulating material is preferred. The insulating material is, for example, a thermoplastic resin, a thermosetting resin, etc. The thermoplastic resin is, for example, polyethylene, polypropylene, polyvinyl chloride, polystyrene, acrylonitrile-butadiene-styrene resin (ABS resin), polyether ether ketone (PEEK), polytetrafluoroethylene (PTFE), polyvinylidene fluoride (PVDF), polyethyleneimine (PEI), polyacetal (POM), modified polyphenylene ether (mPPE), etc. The thermosetting resin is, for example, phenol resin, melamine resin, urea resin, epoxy resin, unsaturated polyester resin, silicone resin, etc. In addition, an insulating material made by filling polyethylene terephthalate (PET) as a main component with short glass fibers and/or inorganic fillers may be used. Such a material may be Unilate (registered trademark) manufactured by Unitika, Ltd. PEEK or mPPE is more preferable as a material of the housing 1, because of their resin properties suitable for the housing 1.

In the example shown in FIG. 1, the irradiator 10 comprises the electrically grounded outer cylinder member 8. For example, the outer cylinder member 8 is an electrically conductive member having a substantially cylindrical shape, and accommodating the first electrode 4 and the second electrode 5 entirely. Due to the outer cylinder member 8 of the irradiator 10, an electric field generated by the irradiator 10 can be suppressed to effectively prevent electric shock to a user handling the irradiator 10. Although not shown, the irradiator 10 may be free of the outer cylinder member 8.

In the example shown in FIG. 1, the irradiator 10 comprises the nozzle 9. The nozzle 9 may be an electrically conductive member or a resin member not having electrical conductivity. When the nozzle 9 has electrical conductivity, the nozzle 9 can suppress electric field generated by the irradiator 10 to effectively prevent electric shock to a user handling the irradiator 10. Although not shown, the irradiator may be free of the nozzle 9. When the irradiator 10 is free of the nozzle 9, the irradiator 10 ejects an active gas from the irradiation opening 5a of the second electrode 5.

In the irradiator 10, a plasma generation gas is supplied from the supply unit 20 to a space between the first electrode 4 and the second electrode 5. In the example shown in FIGS. 3 and 5, the first electrode 4 and the tubular dielectric 3 are spaced apart from each other. In this case, the inner hollow 3a of the tubular dielectric 3 may be used as a flow channel for the plasma generation gas to supply the plasma generation gas to a space between the first electrode 4 and the second electrode 5. Although not shown, when the second electrode 5 is spaced apart from the tubular dielectric 3, a space between the second electrode 5 and the tubular dielectric 3 may be used as a flow channel for the plasma generation gas to supply the plasma generation gas to a space between the first electrode 4 and the second electrode 5.

A method of supplying the plasma generation gas to a space between the first electrode 4 and the second electrode 5 is not specifically limited. Although not shown, a through hole may be provided in the housing 1. In this case, the plasma generation gas supplied to the irradiator 10 through the gas pipeline 30 is supplied to a space between the first electrode 40 and the second electrode 50 through the through hole of the housing 1.

In the invention according to this embodiment, an effect obtained by the fact that the piezoelectric transformer 2, which is a transformer that boosts a voltage applied thereto, is accommodated in the housing to constitute a part of the irradiator 10 is described. Suppose that the transformer is located outside the hosing 1, instead of being accommodated in the housing 1. In this case, the transformer and the first electrode 4 of the irradiator 10 are connected to each other by a wire, so that a high voltage can be applied to the first electrode 4 by using the transformer.

However, in this case, since the transformer is located outside the housing 1, the transformer and the first electrode 4 have to be connected to each other by a sufficiently long wire. The wire connecting the transformer and the first electrode 4 has to be thick to withstand a high voltage boosted by the transformer. Namely, a sufficiently long and thick wire has to be used. A thick wire extending from the irradiator 10 may disturb an operation of the irradiator 10, resulting in impairment of operability of the irradiator 10.

When a high voltage is applied to the wire, the wire functions as a capacitor to accumulate therein energy. In this case, in order to apply a voltage to the first electrode 4, the power source needs to supply excessive power corresponding to the energy accumulated in the wire. When the transformer is located outside the housing 1, the transformer outside the housing 1 and the first electrode 4 have to be connected to each other by a wire, which elongates the length of the wire to which a high voltage boosted by the transformer is applied. When the wire to which a high voltage is applied is long, a significantly large amount energy is accumulated in the wire, whereby the power source needs to supply a significantly large amount of power.

On the other hand, in the invention according to this embodiment, the piezoelectric transformer 2 as a transformer is accommodated in the housing 1 to constitute a part of the irradiator 10. Thus, the length of the conductive wire 50 connecting to the piezoelectric transformer 2 and the first electrode 4 can be shortened. In addition, a voltage which is a low voltage before boosted by the piezoelectric transformer 2 is applied to the voltage supply line 40, which is a long wire extending from the irradiator 10 to the outside of the irradiator 10. Thus, the voltage supply line 40 can be made thinner, which less disturbs an operation of the irradiator 10, thereby improving operability of the irradiator. In addition, since a high voltage is not applied to the voltage supply line 40, accumulation of large amount of energy therein can be suppressed. Thus, power to be supplied by the power source can be lessened.

In the invention according to this embodiment, since the piezoelectric transformer 2 constitutes a part of the irradiator 10, a low voltage before boosted by the piezoelectric transformer 2 is applied to a part of the irradiator 10, the part connecting the piezoelectric transformer 2 and the external power source. Thus, as compared with a case in which the transformer is located outside the irradiator 10, a ratio of a part inside the irradiator 10, to which part a high voltage is applied, can be made smaller. Thus, a protective member, which is provided on the irradiator for preventing electric shock to a user, can be omitted.

Next, an effect of the first electrode 4 connected to the piezoelectric transformer 2 and the second electrode 5 opposed to the first electrode 4 is described. Suppose that the irradiator 10 does not have the first electrode 4 so that a plasma is generated at an end portion of the piezoelectric transformer 2 adjacent to the output area 2b. In this case, the distal end portion of the irradiator 10 positioned on the distal end side has a large thickness in accordance with the thickness of the end portion of the piezoelectric transformer 2 adjacent to the output area 2b. In the example shown in FIG. 3, the thickness of the distal end portion of the irradiator 10 and the thickness of the end portion of the piezoelectric transformer 2 are a dimension of the distal end portion of the irradiator 10 and a dimension of the end portion of the piezoelectric transformer 2 in the radial direction d2. Since the dimension of the piezoelectric transformer 2 has to be determined based on performance required for the piezoelectric transformer 2 as a transformer, it is difficult to make thin the end portion of the piezoelectric transformer 2 so as to make thin the distal end portion of the irradiator 10. The thick distal end portion of the irradiator 10 makes it difficult to use the irradiator 10 in an application that requires the distal end portion of the irradiator 10 be inserted to a narrow space.

In addition, it is required for the irradiator 10 not to damage an irradiation target to be irradiated with an active gas by electric field action of the piezoelectric transformer 2. In particular, when the irradiation target is a person, animal, etc., the irradiation target must not be electrified. In order to suppress damage caused by the electric field action to the irradiation target, it can be considered that an active gas is applied to the irradiation target, with a sufficient distance between the end portion of the piezoelectric transformer 2 and the irradiation target. However, in this case, since a distance between a plasma generation portion and the irradiation target is long, a ratio of the active gas that is deactivated before reaching the irradiation target increases. Alternatively, in order to suppress damage caused by the electric field action to the irradiation target while reducing a distance between the end portion of the piezoelectric transformer 2 and the irradiation target, it can be considered that a grounded electrode is provided around the end portion of the piezoelectric transformer 2. However, in this case, the distal end portion of the irradiator 10 becomes thicker because of the grounded electrode.

On the other hand, the irradiator according to this embodiment comprises the first electrode 4 which is connected to the piezoelectric transformer 2 and to which a voltage is applied from the piezoelectric transformer 2. The thickness of the first electrode 4 can be determined irrespective of the dimension of the piezoelectric transformer 2. Thus, by making thin the first electrode 4 to sufficiently make thin the distal end portion of the irradiator 10, the irradiator 10 can be used in an application which requires the thin distal end portion of the irradiator 10, e.g., an application which requires that the distal end portion of the irradiator be inserted to a narrow space. In addition, since the grounded second electrode 5 is opposed to at least a part of the first electrode 4, damage caused by the electric field action to the irradiation target can be suppressed, and the distal end portion of the irradiator 10 can be made thinner as compared with a case in which a grounded electrode is provided around the end portion of the piezoelectric transformer 2. Since the irradiator 10 has the sufficiently thin distal end portion, the irradiator 10 can be used as an intraoral treatment tool or a dental treatment tool, for example. When the second electrode 5 surrounds the first end portion 4a from a circumference about the axis O1, the second electrode 5 can particularly effectively suppress damage caused by the electric field action to the irradiation target.

The dimension w4 of the first electrode 4 in the radial direction d2 can be suitably determined in consideration of intended use of the active gas irradiation apparatus 100 (namely, a size of the irradiator 10). When the active gas irradiation apparatus 100 is an intraoral treatment tool, the dimension w4 is preferably between 0.5 mm or more and 20 mm or less, more preferably between 1 mm or more and 10 mm or less. When the dimension w4 is equal to or more than the above lower limit value, the first electrode 4 is easy to manufacture. In addition, when the dimension w4 is equal to or more than the above lower limit value, the irradiator 10 can have a sufficiently thin distal end portion. When the dimension w4 is equal to or less than the above upper limit value, a surface area of the first electrode 4 increases so that a plasma can be more efficiently generated to promote cure. When the dimension w4 is equal to or less than the above upper limit value, a plasma can be more efficiently generated to further promote cure, without making excessively larger the irradiator 10.

In the example shown in FIG. 3, the dimension w4 of the first electrode 4 in the radial direction d2 is smaller than the dimension w1 of the piezoelectric transformer 2 in the radial direction d2. This can make thinner the distal end portion of the irradiator 10, as compared with a case in which the irradiator 10 does not have the first electrode 4 so that to plasma is generated at the end portion of the piezoelectric transformer 2.

When the active gas irradiation apparatus 100 is an intraoral treatment tool, a dimension w5 of the second electrode 5 in the radial direction d2 is preferably between 1 mm or more and 15 mm or less, more preferably between 3 mm or more and 6 mm or less.

In the example shown in FIG. 3, the dimension w5 of the second electrode 5 in the radial direction d2 is smaller than the dimension w1 of the piezoelectric transformer 2 in the radial direction d2. This can make thinner the distal end portion of the irradiator 10, while the second electrode 5 is provided, as compared with a case in which the irradiator 10 generates a plasma at the end portion of the piezoelectric transformer 2.

In the example shown in FIG. 3, a dimension w7 of the second portion 1b of the housing 1 in the radial direction d2 is smaller than a dimension w6 of the first portion 1a of the housing 1 in the radial direction d2. When the active gas irradiation apparatus 100 is an intraoral treatment tool, the dimension w7 of the second portion 1b in the radial direction d2 is preferably between 3 mm or more and 20 mm or less, more preferably between 5 mm or more and 10 mm or less. This can make sufficiently thinner the thickness of a part of the irradiator 10 where the second portion 1b is positioned in the axial direction d1.

Next, details of parts of the active gas irradiation apparatus 100 in this embodiment, which are other than the irradiator 10, are described with reference to FIG. 1. The supply unit 20 as shown in FIG. 1 supplies the irradiator 10 with electricity and a plasma generation gas. The supply unit 20 can regulates a voltage and a frequency to be applied to the first electrode 4 through the piezoelectric transformer 2. The supply unit 20 comprises a supply unit housing 21 accommodating the supply source 70. Thus, when the supply source 70 accommodated in the supply unit housing 21 runs out of a gas, the supply source 70 for a plasma generation gas can be replaced with another one.

The supply source 70 supplies a plasma generation gas to a space between the first electrode 4 and the second electrode 5. The supply source 70 is a pressure-resistant container that contains the plasma generation gas. As shown in FIG. 2, the supply source 70 is detachably mounted on a pipe 75 located in the supply unit housing 21. The pipe 75 connects the supply source 70 and the gas pipeline 30. A solenoid valve 71, a pressure regulator 73, a flowrate controller 74, and a pressure sensor 72 (remaining volume sensor) are attached to the pipe 75.

When the solenoid valve 71 is opened, the plasma generation gas is supplied from the supply source 70 to the irradiator 10 through the pipe 75 and the gas pipeline 30. In the illustrated example, an opening degree of the solenoid valve 71 cannot be adjusted, and the solenoid valve 71 is merely turned on or off. However, an opening degree of the solenoid valve 71 may be adjusted. The pressure regulator 73 is located between the solenoid valve 71 and the supply source 70. The present regulator 73 reduces a pressure of the plasma generation gas (depressurizes the plasma generation gas) moving from the supply source 70 toward the solenoid valve 71.

The flowrate controller 74 is located between the solenoid valve 71 and the gas pipeline 30. The flowrate controller 74 regulates a flowrate (supply volume per unit time) of the plasma generation gas having passed through the solenoid valve 71. The flowrate controller 74 regulates a flowrate of the plasma generation gas to 3 L/min, for example.

The pressure sensor 72 detects a remaining volume V1 of the plasma generation gas in the supply source 70. The pressure sensor 72 measures a pressure (remaining pressure) in the supply source 70 as a remaining volume V1. The pressure sensor 72 measures, as a pressure of the supply source 70, a pressure (primary pressure) of the plasma generation gas passing through between the pressure regulator 73 and the supply source 70 (closer to the primary side than the pressure regulator 73). AP-V80 series of KEYENCE Co. (specifically, AP-15S) can be employed as the pressure sensor 72, for example.

An actual remaining volume V1 (cubage) in the supply source 70 is calculated from a remaining pressure measured by the pressure sensor 72 and a capacity (internal volume) of the supply source 70. When a supply source 70 of various capacities are used, a capacity for calculation may be set by selecting an actual capacity of the supply source 70 on a system screen of an input unit, not shown. Alternatively, when a supply source 70 of a constant capacity is used, the control unit 90 may store its capacity in advance.

A joint 76 is provided on an end of the pipe 75, which end is on a side of the supply source 70. The supply source 70 is detachably mounted on the joint 76. By detaching and attaching the joint 76 from and to the supply source 70, the supply source 70 of the plasma generation gas can be replaced with another one, while the solenoid valve 71, the pressure regulator 73, the flowrate controller 74, and the pressure sensor 72 (referred to as "solenoid valve 71 and so on" herebelow) remain fixed in the housing 21. In this case, the solenoid valve 71 and so on can be shared between the current supply source 70 and the replaced supply source 70. The solenoid valve 71 and so on may be fixed to the supply source 70 so as to be detached from the supply unit housing 21 together with the supply source 70.

As shown in FIG. 1, the gas pipeline 30 is a channel through which the plasma generation gas is supplied from the supply unit 20 to the irradiator 10. The gas pipeline 30 is connected to a rear end of the tubular dielectric 3 of the irradiator 10. A material of the gas pipeline 30 is not specifically limited, and a material used for a known gas pipe can be used. The gas pipeline 30 may be a resin pipe or a rubber tube, for example. A flexible material is preferred as a material of the gas pipeline 30.

The voltage supply line 40 is a line that supplies a voltage from the supply unit 20 to the irradiator 10. The voltage supply line 40 is connected to the piezoelectric transformer 2, as described above, and is connected to a foot switch, not shown. A material of the voltage supply line 40 is not specifically limited, and a material used for a known voltage supply line can be used. The voltage supply line 40 may be a metal conducive wire covered with an insulating material.

The control unit 90 as shown in FIG. 2 is formed of an information processing device. Namely, the control unit 90 comprises a CPU (Central Processer Unit), a memory, and an auxiliary storage device connected by a bus. The control unit 90 is operated by executing a program. The control unit 90 may be incorporated in the supply unit 20, for example.

The control unit 90 controls the irradiator 10, the supply unit 20, and the notification unit 80.

A foot switch, not shown, is electrically connected to the control unit 90. When a user of the irradiator 10 operates the foot switch, an electric signal is transmitted from the foot switch to the control unit 90. When the control unit 90 receives the electric signal, the control unit 90 activates the solenoid valve 71 and the flowrate controller 74, and applies a voltage to the first electrode 4.

In this embodiment, every time a user presses the foot switch, the control unit 90 receives the electric signal. Then, the control unit 90 opens the solenoid valve 71 for a predetermined period of time, causes the flowrate controller 74 to regulate a flowrate of the plasma generation gas which has passed through the solenoid valve 71, and applies a voltage to the first electrode 4 for a predetermined period of time. As a result, a certain volume of the plasma generation gas is supplied from the supply source 70 to a space between the first electrode 4 and the second electrode 5, and an active gas is continuously ejected from the nozzle irradiation opening 9a for a certain period of time (e.g., from several seconds to several tens of seconds, 30 seconds in this embodiment).

Namely, in this embodiment, an ejection volume of the active gas per one press of the foot switch by a user is fixed. Such an operation for ejecting the active gas of the predetermined ejection volume is referred to as a unit operation. In this embodiment, the unit operation is one pressing of foot switch by a user. An ejection volume of the active gas per unit operation (a supply volume of the plasma generation gas from the supply source 70 to a space between the first electrode 4 and the second electrode 5 per unit operation) may be a fixed value that is previously set or a variable value that can be set by operating an operation panel, not shown.

The control unit 90 computes as remaining information at least one of a remaining number of times N and a remaining time T of the plasma generation gas. In this embodiment, the control unit 90 computes as the remaining information only the remaining number of times N among the remaining number of times N and the remaining time T. The remaining number of times N is a number of times of the unit operations to be left during which the plasma generation gas can be supplied from the supply source 70 to a space between the first electrode 4 and the second electrode 5. The remaining time T is a time to be left during which the plasma generation gas can be supplied from the supply source 70 to a space between the first electrode 4 and the second electrode 5.

Both the remaining time N and the remaining time T can be calculated from the remaining volume V1 of the plasma generation gas in the supply source. The remaining number of times N can be calculated (N=V1/V2) based on the remaining volume V1 and a supply volume V2 of the plasma generation gas per unit operation of the foot switch. Alternatively, the remaining number of times N is calculated by computing an average value V2 (average value) of usages (supplies) of the plasma generation gas over the last several times, and by dividing the remaining volume V1 of the plasma generation gas by the average value V2 (average value). The remaining time T can be calculated (T=V1/V3) based on the remaining volume V1, and a supply volume V3 of the plasma generation gas supplied from the supply source 70 to a space between the first electrode 4 and the second electrode 5 per unit time.

The notification unit 80 gives a notice of at least one of the remaining number of times N and the remaining time T. In this embodiment, the notification unit 80 displays the number of times N. The notification unit 80 displays the remaining number of times N calculated by the control unit 90 by a numeric character. A display unit capable of displaying a numeric character or a mechanical counter may be employed as the notification unit 80.

In the illustrated example, the notification unit 80 is integrated in the supply unit housing 21 on an outer surface thereof. However, the notification unit 80 may be independent from the supply unit 20. The notification unit 80 may display the remaining number of times N by a way different from a numerical character. For example, an analogue display structure formed of a dial and a needle may be employed as the notification unit 80. Further, the notification unit 80 may give a notice of the remaining number of times N by displaying a color or by turning on/off light.

Further, the notification unit 80 may give a notice of the remaining number of times N by sound. In this case, a speaker can be employed as the notification unit 80, for example.

As in this embodiment, when a certain volume of the plasma generation gas is supplied from the supply source 70 to a space between the first electrode 4 and the second electrode 5 upon pressing of the foot switch by a user, to give a notice of the remaining number of times N is more convenient for a user than to give a notice of the remaining time T.

Next, a method of using the active gas irradiation apparatus 100 is described. A user such as a doctor moves the irradiator 10 by hand and directs the nozzle irradiation opening 9a toward an irradiation target described later. Under this state, the user presses the foot switch to supply electricity and a plasma generation gas from the supply source 70 to the irradiator 10. The plasma generation gas supplied to the irradiator 10 flows from the rear end of the tubular dielectric 3 into the inner hollow 3a of the tubular dielectric 3. The plasma generation gas is ionized at a position where the first electrode 4 and the second electrode 5 are opposed to each other to become a plasma.

In this embodiment, the first electrode 4 and the second electrode 5 are opposed to each other in a direction orthogonal to the direction along which the plasma generation gas flows. The plasma, which was generated at the position where outer circumferential surface of the first electrode 4 and the inner circumferential surface of the second electrode 5 are opposed to each other, changes the composition of the gas to become an active gas containing active species such as radical, while flowing through the inner hollow 3a of the tubular dielectric 3.

The active gas thus generated is ejected from the nozzle irradiation opening 9a. The ejected active gas further activates a part of the gas near the nozzle irradiation opening 9a to generate active species. The active gas containing these active species is applied to the irradiation target.

The irradiation target may include, for example, cells, living tissues, biological individuals, etc. The living tissues may include, for example, respective organs such as viscera, epithelial tissues covering body surfaces and inner surfaces of body cavities, periodontal tissues such as gingiva, alveolar bone, periodontal ligament and cementum, teeth, bones, etc. The biological individuals may be any mammals such as humans, dogs, cats, pigs, etc.; birds; fish, etc.

The plasma generation gas may be, for example, rare gases such as helium, neon, argon, krypton, etc.; nitrogen, etc. One of these gases may be used solely or two or more gases may be used in combination. The plasma generation gas preferably contains nitrogen as a main component. Herein, a gas containing nitrogen as a main component means that a nitrogen content in the plasma generation gas is more than 50% by volume. Namely, the nitrogen content in the plasma generation gas is preferably more than 50% by volume, more preferably 70% by volume, and particularly preferably between 90% by volume and 100% by volume. A gas component in the plasma generation gas, other than nitrogen, is not specifically limited, and may be, for example, oxygen, rare gas, etc.

When the active gas irradiation apparatus 100 is an intraoral treatment tool, an oxygen concentration of the plasma generation gas to be introduced to the tubular dielectric 3 is preferably 1% by volume or less. When the oxygen concentration is equal to or less than the upper limit value, generation of ozone can be reduced.

A flowrate of the plasma generation gas to be introduced to the tubular dielectric 3 is preferably between 1 L/ruin and 10 L/min. When the flowrate of the plasma generation gas to be introduced to the tubular dielectric 3 is equal to or more than the lower limit value, increase in temperature of an irradiation surface of the irradiation target can be easily suppressed. When the flowrate of the plasma generation gas is equal to or less than the upper limit value, purification, activation or cure of the the irradiation target can be further promoted.

A temperature of the active gas applied from the nozzle irradiation opening 9a is preferably 50° C. or less, more preferably 45° C. or less, further preferably 40° C. or less. When the temperature of the active gas applied from the nozzle irradiation opening 9a is equal to or less than the upper limit value, it is easy for the irradiation surface to have a temperature of 40° C. or less. When the irradiation surface has a temperature of 40° C. or less, stimulus to an affected area as the irradiation part can be reduced. A lower limit value of the temperature of the active gas applied from the nozzle irradiation opening 9a is not specifically limited, and is 10° C. or more, for example. The temperature of the active gas is a value of the temperature of the active gas, which is measured at the nozzle irradiation opening 9a by a thermocouple.

A distance (irradiation distance) from the nozzle irradiation opening 9a to the irradiation surface is preferably between 0.01 mm and 10 mm, for example. When the irradiation distance is equal to or more than the above lower limit value, the temperature of the irradiation surface can be lowered to further mitigate stimulus to the irradiation surface. When the irradiation distance is equal to or less than the above upper limit value, an effect such as cure can be further enhanced.

A temperature of the irradiation surface at a position distant from the nozzle irradiation opening 9a by between 1 mm or more and 10 mm or less is preferably 40° C. or less. When the irradiation surface has a temperature of 40° C. or less, stimulus to the irradiation surface can be reduced. A lower limit value of the temperature of the irradiation surface is not specifically limited, and is 10° C. or more, for example. The temperature of the irradiation surface can be adjusted by controlling an alternating voltage applied to a space between the first electrode 4 and the second electrode 5, an ejection volume of the active gas to be applied, a way from the distal end 4d of the first electrode 4 to the nozzle irradiation opening 9a, etc. in combination. The temperature of the irradiation surface can be measured by using a thermocouple.

Active species (radical, etc.) contained in the active gas may include, for example, hydroxyl radical, singlet oxygen, ozone, hydrogen peroxide, superoxide anion radical, nitrogen monoxide, nitrogen dioxide, peroxynitrite, nitrous peroxide, dinitrogen trioxide, etc. A type of active species contained in the active gas can further adjusted to a type of the plasma generation gas.

A hydroxyl radical density (radical density) in the active gas in the active gas is preferably between 0.1 µmol/L and 300 µmol/L. When the radical density is equal to or more than the lower limit value, purification, activation, or cure of the irradiation target selected from cells, living tissues and biological individuals, can be further promoted. When the radical density is equal to or less than the upper limit value, stimulus to the irradiation surface can be reduced.

The radical density can be measured by the following method, for example. 0.2 mL of DMPO (5,5-dimethyl-1-pyrroline-N-oxide) 0.2 mol/L solution is irradiated with the active gas for 30 seconds. At this time, a distance from the nozzle irradiation opening 9a to a liquid level is 5.0 mm. A hydroxyl radical concentration of the solution irradiated with the active gas is measured using an electron spin resonance (ESR) method. The obtained value is the radial density.

A singlet oxygen density in the active gas is preferably between 0.1 µmol/L and 300 µmol/L. When the singlet oxygen density is equal to or more than the lower limit value, purification, activation and cure of the irradiation target such as cells, living tissues, biological individuals, etc. can be easily promoted. When the singlet oxygen is equal to or less than the upper limit value, stimulus to the irradiation surface can be reduced.

The singlet oxygen density can be measured by the following method, for example. 0.4 mL of TPC (2,2,5,5-tetramethyl-3-pyrroline-3-carboxamide) 0.1 mol/L solution is irradiated with the active gas for 30 seconds. At this time, a distance from the nozzle irradiation opening 9a to a liquid level is 5.0 mm. A singlet oxygen concentration of the solution irradiated with the active gas is measured using an electron spin resonance (ESR) method. The obtained value is the singlet oxygen density.

A flowrate of the active gas applied from the nozzle irradiation opening 9a is preferably between 1 L/min and 10 L/min. When the flowrate of the active gas applied from the nozzle irradiation opening 9a is equal to or more than the lower limit value, an effect of the active gas acting on the irradiation surface can be sufficiently increased. When the flowrate of the active gas applied from the nozzle irradiation opening 9a is less than the upper limit value, a temperature of the irradiation surface irradiated with the active gas can be prevented from excessively increasing. In addition, when the irradiation surface is wet, rapid dry of the irradiation surface can be prevented. Further, when the irradiation surface is an affected area, stimulus to a patient can be suppressed. In the active gas irradiation apparatus 100, a flowrate of the active gas applied from the nozzle irradiation opening 9a can be adjusted by a volume of the plasma generation gas supplied to the tubular dielectric 3.

The active gas generated by the active gas irradiation apparatus 100 has an effect of promoting cure of traumatic injuries and abnormalities. By applying the active gas to cells, living tissues, or biological individuals, purification and/or activation of the irradiated portion, or cure of the irradiated portion can be promoted.

When the active gas is applied in order to promote cure of traumatic injuries and/or abnormalities, there is no particular limitation on a frequency of irradiation, a number of times of irradiation, and a period of irradiation. For example, when an affected area is irradiated with the active gas with an irradiation volume between 1 L/min and 5.0 L/min, irradiation conditions of once to five times a day, for 10 seconds to 10 minutes each time, over a day to 30 days, etc. are preferred from the viewpoint of promoting cure.

The active gas irradiation apparatus 100 in this embodiment is particularly useful as an intraoral treatment tool and dental treatment tool. In addition, the active gas irradiation apparatus 100 in this embodiment is suitable as an animal treatment tool.

In the above, one embodiment has been described with reference to the specific example, but the above specific example does not intend to limit the embodiment. The aforementioned one embodiment can be carried out in various other specific examples, and can be variously omitted, replaced and modified without departing from its scope.

Modification examples are described herehelow with reference to the drawings. In the below description and the drawings used for the below description, the same reference numerals as those used for the corresponding parts in the specific example described above are used for parts that can be configured in the same way as in the specific examples described above, and redundant description is omitted.

In the aforementioned embodiment, the example in which the first electrode 4 has a columnar shape is described. However, the shape of the first electrode 4 is not limited thereto. As an example, the first electrode 4 has a prismatic shape, in particular, a rectangular columnar shape. In this case, a plasma can be generated by the first electrode 4 near the first end portion 4a of the first electrode 4, which is as follows. When a voltage is applied to the first electrode 4, a particularly high voltage is generated at a corner of the first electrode 4, which corner is positioned near the first end portion 4a. Thus, a gas around the corner can be ionized to generate a plasma. As another example, the first electrode 4 may have a needle-like shape with the first end portion 4a being pointed. In this case, since a particularly high voltage is locally generated at the pointed first end portion 4a of the first electrode 4, a plasma can be generated around the first end portion 4a. Depending on conditions of a shape of the first electrode 4 or a voltage to be applied to the first electrode 4, a plasma can be generated around the first end portion 4a of the first electrode 4. When the first electrode 4 can generate a plasma near the first end portion 4a, the irradiator 10 may be free of the second electrode 5.

In the aforementioned embodiment, the example in which the irradiator 10 comprises the first buffer 7b provided between the piezoelectric transformer 2 and the piezoelectric transformer casing 7a is described. However, although not shown, the irradiator 10 may be free of the first buffer 7b.

In the aforementioned embodiment, the example in which the irradiator 10 comprises the conductive wire 50, and the first electrode 4 is connected to the output area 2b of the piezoelectric transformer 2 through the conductive wire 50 is described. However, the method of connecting the first electrode 4 to the output area 2b of the piezoelectric transformer 2 is not limited thereto. As another example, the first electrode 4 is connected to the output area 2b of the piezoelectric transformer 2 by soldering.

The irradiator 10 may comprise one piezoelectric transformer 2 or may comprise a plurality of piezoelectric transformers 2. When the irradiator 10 comprises a plurality of piezoelectric transformers 2, the plurality of piezoelectric transformers 2 may be accommodated in one housing 1. When the irradiator 10 comprises a plurality of piezoelectric transformers 2, each of the piezoelectric transformers 2 are connected to the first electrode 4, and a voltage is applied thereto from the plurality of piezoelectric transformers 2.

The following effect can be obtained by applying voltages from the plurality of piezoelectric transformers 2 to the first electrode 4. Even when a capacity of each of the plurality of piezoelectric transformers 2 is small, a sufficient amount of plasma can be generated between the first electrode 4 and the second electrode 5. In addition, as compared with a case in which a voltage is applied to the first electrode 4 from one piezoelectric transformer 2 with a large capacity, a current flowing through each of the plurality of piezoelectric transformers 2 can be made smaller. In other words, a current can be distributed to the respective piezoelectric transformers 2.

In the irradiator 10, a dimension w8 of a part in the axial direction d1 where the first electrode 4 and the second electrode 5 are opposed to each other may be, in particular, between more than 3 mm and less than 20 mm. When the dimension w8 is less than 20 mm, increase in a current of electric discharge generated between the first electrode 4 and the second electrode 5 can be suppressed. Thus, mechanical damage of the piezoelectric transformer 2 caused by a large current can be more effectively suppressed. In addition, when the dimension w8 is more than 3 mm, a plasma can be generated sufficiently efficiently between the first electrode 4 and the second electrode 5 so that a sufficient amount of active species can be generated. Thus, a sufficient amount of active species can be applied to an irradiation target by using the irradiator 10. As a result, when the irradiator 10 is used as a treatment tool, a particularly sufficient treatment effect can be obtained. From the viewpoint of further improving the above effect, the dimension w8 is further preferably between more than 5 mm and less than 15 mm.

In the irradiator 10, a distance w9 in the axial direction d1 between the part of the first electrode 4, which part is opposed to the second electrode 5, and the output area 2b of the piezoelectric transformer 2 may be, in particular, between more than 1 mm and less than 100 mm. An effect obtained by the distance w9 less than 100 mm is described. Between the part of the first electrode 4, which part is opposed to the second electrode 5, and the output area 2b of the piezoelectric transformer 2, a transmission portion is positioned, the transmission portion transmitting a voltage from the output area 2b of the piezoelectric transformer 2 to the part of the first electrode 4, which part is opposed to the second electrode 5. For example, in the example shown in FIG. 3, a part of the first electrode 4, which part is closer to the part opposed to the second electrode 5 to the piezoelectric transformer 2, and the conductive wire 50 correspond to the transmission portion. When a voltage is applied from the piezoelectric transformer 2 to the part of the first electrode 4, which part is opposed to the second electrode 5, the voltage is also applied to the transmission portion. In this case, the transmission portion functions as a capacitor to accumulate therein energy. Thus, it is necessary to supply excessive power corresponding to the energy accumulated in the transmission portion, in order to apply a voltage to the part of the first electrode 4, which part is opposed to the second electrode 5. In other words, it is necessary to supply larger power by a stray capacitance of the transmission portion. In this case, it may be necessary to increase a current flowing through the piezoelectric transformer 2. On the other hand, when the distance w9 is less than 100 mm, the length of the transmission portion in the axial direction d1 can be reduced. Thus, a stray capacitance of the transmission portion can be reduced, and a sufficient voltage can be applied to the part of the first electrode 4, which part is opposed to the second electrode 5, without increasing a current flowing through the piezoelectric transformer 2. From the viewpoint of further improving the above effect, the distance w9 is further preferably between 1 mm or more and 40 mm or less.

A distance w10 in the axial direction d1 between the end of the second electrode 5, which is provided with the irradiation opening 5a and the first portion 1a of the housing 1, which accommodates the piezoelectric transformer 2, may be, in particular, more than 10 mm and less than 150 mm. An effect of w10 which is between more than 10 mm and less than 150 mm is described. The irradiator 10 is supposed to be used as an intraoral treatment tool or a dental treatment tool. The distance w10 corresponds to a length of a part which is close to the irradiation opening 5a to the first portion 1a accommodating the piezoelectric transformer 2 of the irradiator 10, the part being designed as being thin irrespective of the dimension of the piezoelectric transformer 2. When the length of the part is between more than 10 mm and less than 150 mm, it is sufficiently easy to insert the distal end portion of the irradiator 10 into a mouth and to operate the irradiator 10. From the viewpoint of improving the above effect, the distance w10 is further preferably between more than 30 mm and less than 50 mm.

The aspect of the present invention is not limited to the aforementioned respective embodiments, and includes various modifications conceivable to those skilled in the art. The effect of the present invention is also not limited to the aforementioned contents. Namely, various additions, modifications and partial deletions are possible without departing from the conceptual idea and purpose of the invention derived from the content defined in the claims and their equivalents.

The invention claimed is:

1. An irradiator comprising:
    a piezoelectric transformer accommodated in a housing;
    a first electrode connected to the piezoelectric transformer, to which a voltage is applied from the piezoelectric transformer; and
    an irradiation opening that ejects at least one of a plasma generated by the first electrode and an active gas generated by the plasma;
    wherein at least a part of the first electrode is located between the piezoelectric transformer and the irradiation opening; and
    the first electrode has a dimension smaller than a dimension of the piezoelectric transformer, in a radial direction perpendicular to an axis of the first electrode.

2. The irradiator according to claim 1, comprising a second electrode opposed to at least a part of the first electrode.

3. The irradiator according to claim 2, wherein the second electrode surrounds the first electrode from a circumference about an axis of the first electrode.

4. The irradiator according to claim 3, wherein:
    the first electrode has a first end portion positioned oppositely to an end portion connected to the piezoelectric transformer, in a direction in which the axis of the first electrode extends; and
    the second electrode surrounds the first end portion from the circumference about the axis of the first electrode.

5. The irradiator according to claim 2, wherein the second electrode has a dimension larger than a dimension of the first electrode, in a direction in which an axis of the first electrode extends.

6. An irradiator comprising:
    a piezoelectric transformer accommodated in a housing;
    a first electrode connected to the piezoelectric transformer, to which a voltage is applied from the piezoelectric transformer;
    an irradiation opening that ejects at least one of a plasma generated by the first electrode and an active gas generated by the plasma; and
    a second electrode opposed to at least a part of the first electrode;
    wherein at least a part of the first electrode is located between the piezoelectric transformer and the irradiation opening; and
    the second electrode has a dimension smaller than a dimension of the piezoelectric transformer, in a radial direction perpendicular to an axis of the first electrode.

7. A plasma apparatus comprising:
    an irradiator according to claim 1;
    a power source that applies a voltage to the piezoelectric transformer; and
    a voltage supply line connecting the piezoelectric transformer and the power source.

8. A plasma apparatus comprising:
    an irradiator according to claim 6;
    a power source that applies a voltage to the piezoelectric transformer; and
    a voltage supply line connecting the piezoelectric transformer and the power source.

* * * * *